Figure 1:
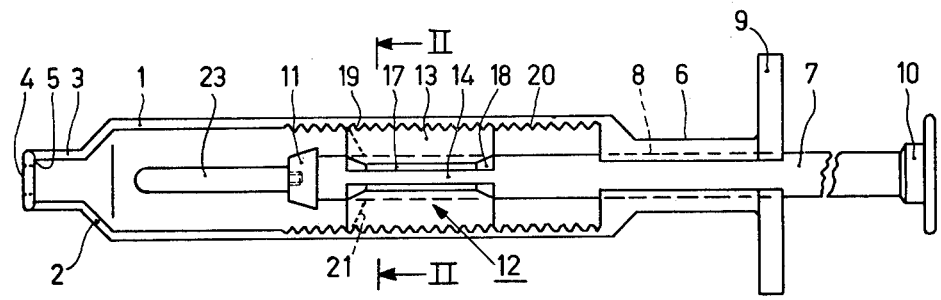

United States Patent [19]

van Vroenhoven

[11] 4,006,849
[45] Feb. 8, 1977

[54] INJECTION SYRINGE HOLDER HAVING A BLOCKING MEMBER

[75] Inventor: Petrus Adrianus Wilhelmus Hendrik van Vroenhoven, Eindhoven, Netherlands

[73] Assignee: U.S. Philips Corporation, New York, N.Y.

[22] Filed: Oct. 2, 1975

[21] Appl. No.: 619,071

[30] Foreign Application Priority Data

Oct. 31, 1974 Netherlands ............... 7414218

[52] U.S. Cl. .................. 222/309; 128/218 D
[51] Int. Cl.² ........................ A61M 5/315
[58] Field of Search .......... 222/309, 325, 326, 327; 128/218 R, 219, 220, 218 D

[56] References Cited

UNITED STATES PATENTS

| 2,345,302 | 3/1944 | Smith | 128/218 D |
| 2,665,688 | 1/1954 | Hyslop | 128/218 D |

Primary Examiner—Stanley H. Tollberg
Attorney, Agent, or Firm—Frank R. Trifari

[57] ABSTRACT

A holder for an injection syringe which can accommodate cartridges of different length and diameter. The holder contains a channel-shaped body provided at one end with a guide member for a plunger rod and at the other end with a shoulder. A blocking member is movable in the holder to center and hold the cartridge against the shoulder.

5 Claims, 7 Drawing Figures

INJECTION SYRINGE HOLDER HAVING A BLOCKING MEMBER

The invention relates to a holder for an injection syringe, which comprises a channel-shaped body, which at one end is provided with a guide member for a plunger rod as well as a plunger rod which via the guide member extends into the channel-shaped body, and which at the other end is provided with a shoulder.

Such a holder is known from British Pat. specification No. 886,444.

A cartridge which is fitted in said holder according to FIGS. 1–4 of said patent specification is fixed at the front of the holder in such a way that an undesired longitudinal movement of the cartridge in the holder is impossible. Movement in a vertical direction remains possible, but according to FIG. 5 of said patent specification this can be prevented by providing the holder at the rear end with a resilient catch which can snap around the rear edge of the cartridge.

This last-mentioned construction has the drawback that the holder is only suited for use of cartridges with a specific length dimension. For all embodiments of the known holder the diameter of the cartridges to be used in the holder should not or not substantially vary.

The applicant has developed a holder of the type mentioned in the preamble which does not have the afore-mentioned drawbacks.

According to the invention the channel-shaped body contains a blocking member in line with the guide member, which blocking member is movable inside the channel-shaped body and is provided with a passage for the plunger rod.

The holder according to the invention accepts cartridges of different longitudinal dimensions and different diameter. When a cartridge is fitted into the holder, it is moved forwards with the aid of the movable blocking member until the front of the cartridge butts against the shoulder of the channel-shaped body. The ampoule is then firmly locked between the shoulder and the blocking member, so that a further movement of the ampoule either in the longitudinal or in the transverse direction is no longer possible.

Different embodiments of the blocking member are possible. For example, said member may consist of a disc which is disposed in the channel-shaped body, which disc is perpendicular to the longitudinal direction of the channel-shaped body and is provided with an opening for passage of the plunger rod. At the upper side the disc may be provided with a bracket which tightly grips around the top edge or outer wall of the channel-shaped body.

In a preferred embodiment the blocking member is a sliding piece which is disposed in the channel-shaped body, which piece engages an inner sidewall portion of the channel-shaped body with a part of the outer piece wall surface.

Preferably the sliding piece is provided with teeth at the outer wall, which mesh with teeth disposed at the inner wall of the channel-shaped body.

In a further preferred embodiment the sliding piece is provided with a central longitudinal slot whose lower part constitutes a feed-through passage for the plunger rod, at least one of the resilient members disposed at either side of the slot being provided with the teeth. By compressing the resilient members the teeth are disengaged, so that the sliding piece can readily be moved within the channel-shaped body.

In a particularly advantageous embodiment the sliding piece comprises one or two resilient tag-shaped elements which can engage with grooves which are formed in the outer wall of the sliding piece, the tag-shaped elements being provided with teeth at the sides which face the channel-shaped body, in such a way that when an inwardly directed force is exerted on the elements, these elements are fully accommodated in the recesses, the teeth of the elements being disengaged from the teeth provided at the channel-shaped body.

In the two last-mentioned embodiments the teeth may have a sawtooth profile, the teeth passing over each other as the sliding piece is slid forward and sliding back being possible only by moving the resilient members or tag-shaped elements inwards and thus disengaging the teeth.

Furthermore, the sliding piece in the holder according to the invention may be provided with a longitudinal ridge at the underside, which ridge engages with a slot which is formed in the bottom of the channel-shaped body.

These steps ensure that the sliding piece is centered in the channel-shaped body and cannot become detached from the holder, for example during transportation.

In a preferred embodiment of the holder according to the invention the head face of the sliding piece, i.e. the surface which faces towards the front of the holder, has a concave or convex profile, or a conical shape. When such a holder is used, the cartridge is automatically centered in the channel-shaped body when the slide piece is pressed home, owing to said shape of the head face. Especially in the case of cartridges of comparatively small diameter such a centering is a great practical advantage.

Figure 2:
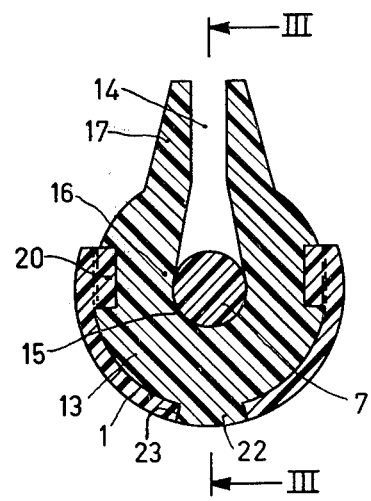
Figure 3:
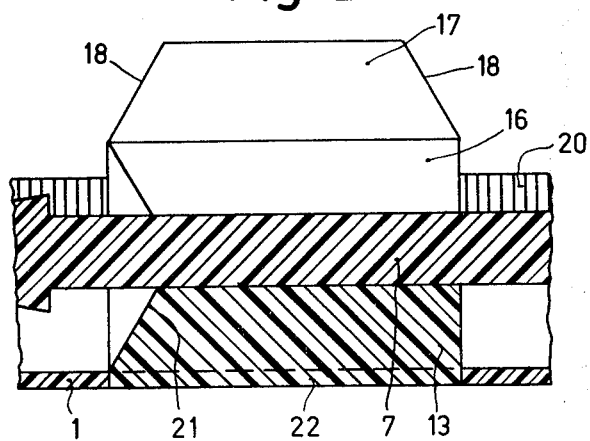
Figure 4:
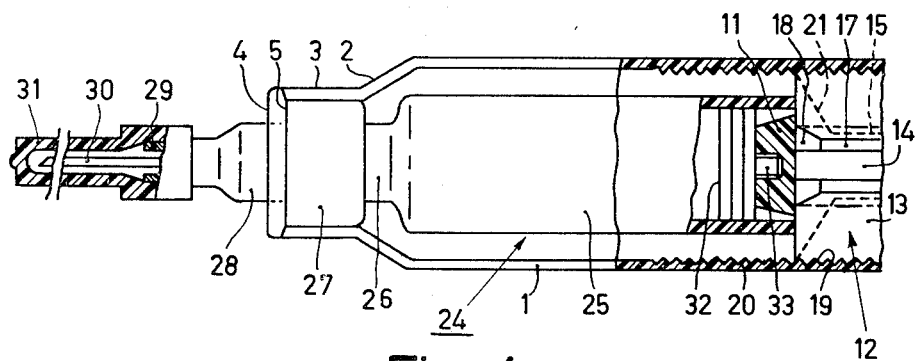
Figure 6:
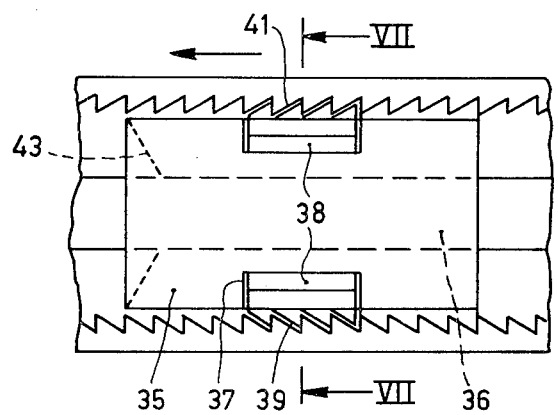
Figure 7:
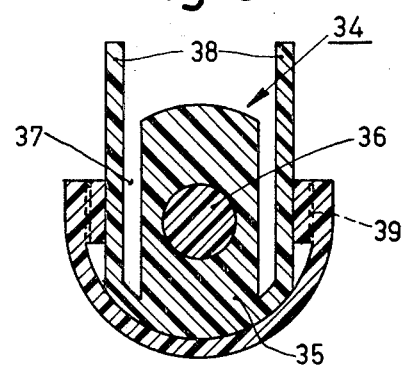
Figure 5:
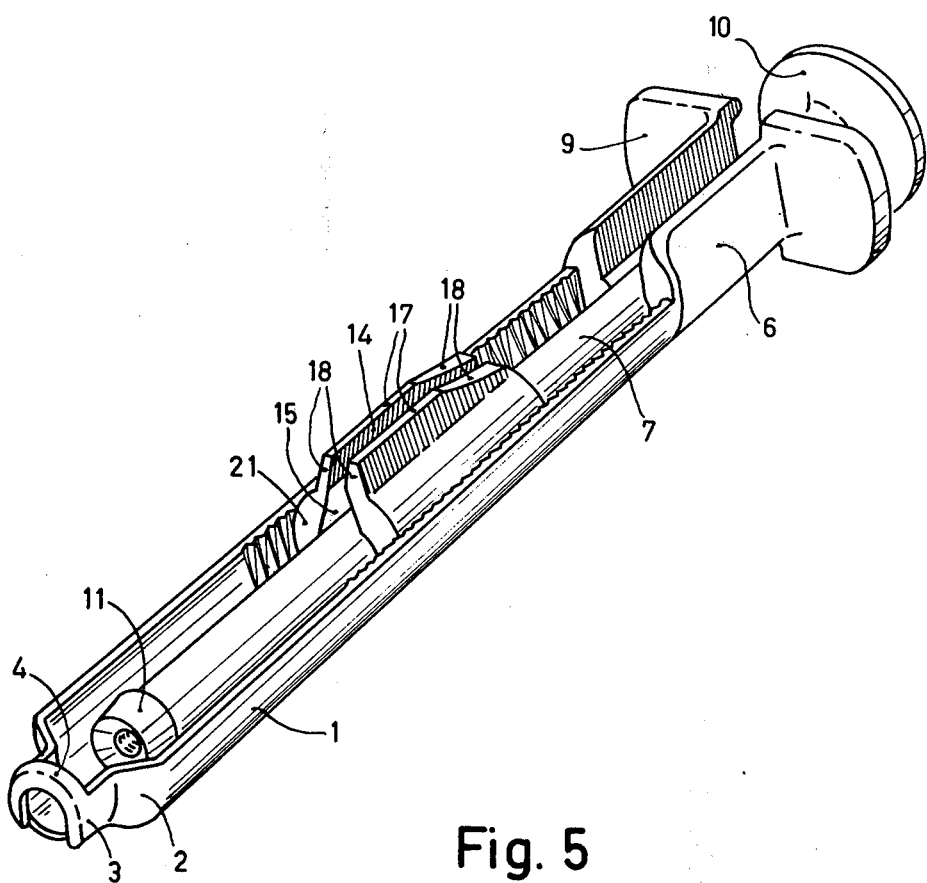

The invention will be described in more detail with reference to the accompanying drawings, in which FIG. 1 is a top view of a holder according to the invention, FIG. 2 is a cross-section of the holder of FIG. 1 taken on the line II—II, FIG. 3 is a longitudinal section of a part of the holder of FIG. 1 taken on the line III—III of FIG. 2, FIG. 4 is a top view, part sectional view of the holder of FIG. 1 in which a cartridge is fitted, FIG. 5 is a perspective view of the holder of FIG. 1, FIG. 6 is a top view of a part of a holder according to the invention in which a different sliding piece is used, and FIG. 7 is a cross-section taken on the line VII—VII in FIG. 6.

In FIGS. 1–5 the reference numeral 1 denotes a channel-shaped body which at the front comprises a tapered portion 2 which adjoins a neck portion 3. Neck portion 3 is provided with a ring 4 which, as can be seen in FIG. 5, is open at the underside. The internal diameter of the ring 4 is smaller than that of the neck portion 3, so that between these parts a shoulder 5 is formed. At the rear the body 1 is provided with a guide member 6 for a plunger rod 7. Said guide member 6 is open at the top and is furthermore provided with a central duct 8 through which the plunger rod 7 extends. At the rear the body 6 comprises a grip 9. The plunger rod is provided with an actuation knob 10 at the rear and with a coupling facility at the front, preferably by means of a threaded hole formed in a head 11. The channel-shaped body 1 further comprises a blocking member which is denoted by the reference numeral 12 which takes the form of a sliding piece 13 which is movable inside the channel-shaped body. The sliding piece 13 is provided with a longitudinal slot 14 whose lower part 15 (see FIGS. 2 and 3) forms a lead-through passage for the plunger rod 7. The wall portions 16 (see FIGS. 2 and 3) of sliding piece 13 which are disposed at either side of the longitudinal slot 14 are resilient and at the upper side they are provided with raised edges 17 which have bevelled parts 18 at the ends. The edges 17 with bevelled parts 18 form a grip for moving sliding piece 13. The wall portions 16 at the wall which faces the channel-shaped body 1 are provided with teeth 19 which mesh with the teeth 20 which are disposed at the inner wall of the channel-shaped body 1. The head face 21 of the sliding piece 13 which is directed towards the front of the holder has a conical shape. The lower end of the sliding piece 13 is provided with a longitudinal ridge 22 (see FIGS. 2 and 3), of preferably trapezoid cross-section, which engages with a slot 23 formed in the bottom of channel-shaped body 1.

When the sliding piece 13 is moved for example a forwardly directly force is exerted on the bevelled part 18. As a result of the spring force of wall portions 16 and also owing to the fact that the complete holder is made of a somewhat elastic material such as plastic, the teeth 19 and 20 will pass over each other and the sliding piece 13 will advance. In a similar way a backward movement of the sliding piece 13 is possible. The movement of the sliding piece can be facilitated by moving the wall portions 16 towards each other, the teeth 19 of sliding piece 13 then being disengaged from the teeth 20 of the channel-shaped body 1. In the extreme positions of the sliding piece 13 ridge 22 butts against the end of slot 23.

The cartridge 24 shown in FIG. 4 is of a conventional type such as for example described in U.S. Pat. No. 3,695,478. Cartridge 24 consists of an ampoule 25 filled with a liquid medicament, which is provided with a neck portion 26 and an adjoining collar 27. Collar 27 is connected to a needle mount 28 which contains a sleeve 29 with secured therein a sharp needle 30. Around needle 30 a needle guard 31 is disposed which is frictionally secured onto needle sleeve 29. At the end which is remote from the needle the ampoule 25 contains a plunger 32 which is movable therein and which is provided with a connection facility for the plunger rod 7, for example by means of a threaded connection 33 which engages the thread formed in part 11.

Cartridge 24 can readily be inserted in the holder according the invention. For this, the needle holder 28 with needle 30 and needle guard 31 is inserted through the ring 4 of channel-shaped body 1, which ring is open at the lower side (also see FIG. 5) and subsequently the ampoule 25 is pressed into the channel-shaped body 1. Then the sliding piece 13 is slid forward in the manner described hereinbefore. The conical head face 21 of sliding piece 13 then presses against the rear of ampoule 25, so that ampoule 25 is centered in channel-shaped body and is also pushed forwards. Said movement stops when the front of collar 27 butts against shoulder 5 of ring 4. If subsequently head 11 of plunger rod 7 is secured to connection 33 of plunger 32, the situation of FIG. 4 is obtained and after removal of the needle guard the holder with cartridge is ready for administering an injection. The needle is then inserted into the patient's body and subsequently the plunger rod 7 is pushed forwards so that plunger 32 moves inside the ampoule 25 and the medicament enters the patient's body via the needle. During insertion of the needle the backward force exerted on the needle is smaller than the force which is required to allow the teeth 19 of sliding piece 13 to move over the teeth 20 of the channel-shaped body 1.

FIGS. 6 and 7 relate to an embodiment of a holder according to the invention which differs from the embodiment shown in FIGS. 1–5 in respect of the sliding piece and the teeth. FIG. 6 shows a top view of that part of the holder which comprises the different sliding piece and teeth. FIG. 7 is a cross-section of the holder of FIG. 6 taken at the line VII—VII.

In FIGS. 6 and 7 the modified sliding piece is generally denoted by the reference numeral 34. The sliding piece 34 substantially consists of a cylindrical member 35 which has a central duct 36 for the passage of the plunger rod 7.

At either side of duct 36 the member 35 has two grooves 37 which are perpendicular to the axis of the member 35. Two resilient tag-shaped elements 38 which are connected to the member 35 extend in said grooves. The elements 35 are provided with teeth 39 with a sawtooth profile 40 at the side which is remote from the axis of the member 35. The teeth 39 engage the teeth 41 of the channel-shaped body 1. The teeth 41 also have a sawtooth profile 42. By exerting a force on the sliding piece 34 in accordance with the direction of the arrow indicated in FIG. 6, the teeth 39 and 41 will pass over each other owing to the resilience of the tag-shaped elements 38, thus allowing a movement of the sliding piece in the direction of the arrow. A backward movement of the sliding piece 34, i.e. in the direction opposite to the direction of the arrow, is not directly possible. For this, the tag-shaped elements 38 must be moved towards each other (pressed together), the teeth 39 then being disengaged from the teeth 41 of the channel-shaped body 1. The head face 43 of sliding piece 34 has a conical shape so that the cartridge to be used in the holder of FIGS. 6 and 7 is automatically centred in the channel-shaped body 1 when the sliding piece 34 is slid forward. The sawtooth profile shown in FIGS. 6 and 7 has the advantage that the sliding piece is blocked in the backward direction, so that during an injection a backward movement of the ampoule which is contained in the holder is definitely excluded.

What is claimed is:

1. A holder for an injection syringe, comprising a channel-shaped body having two ends, and at least sidewall portions extending longitudinally between said ends, a guide member at one end having a passage, and a shoulder at the other end, a plunger rod extending through said guide member passage into the channel-shaped body; and a blocking member arranged between and engaging said sidewall portions for longitudinal translational sliding movement, wherein a sidewall portion has teeth along an inner wall surface, and said blocking member comprises teeth engaging the teeth of the sidewall portion.

2. A holder as claimed in claim 1 wherein said blocking member comprises a sliding piece having a central longitudinal slot forming a lead-through passage for the plunger rod and having resilient parts disposed at either side of the slot, said blocking member teeth being provided on said resilient parts.

3. A holder as claimed in claim 1 wherein said blocking member comprises a sliding piece having a groove formed in an outer wall of the piece, and a resilient tag-shaped element on which blocking member teeth are formed, said element being arranged to be accommodated in said groove in response to an inwardly directed force exerted on the element so as to disengage said teeth.

4. A holder as claimed in claim 1 wherein said body has a longitudinal slot between said sidewall portions, and said blocking member comprises a ridge engaging said slot.

5. A holder as claimed in claim 4 wherein said blocking member has a face, at a member end toward said shoulder, having means for centering an injection ampoule placed in the holder.

* * * * *